US00PP30459P3

(12) United States Plant Patent
Klemm et al.

(10) Patent No.: US PP30,459 P3
(45) Date of Patent: Apr. 30, 2019

(54) ***PELARGONIUM* PLANT NAMED 'KLEPZ17487'**

(50) Latin Name: *Pelargonium zonale*
Varietal Denomination: KLEPZ17487

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,935

(22) Filed: May 23, 2018

(65) Prior Publication Data

US 2018/0343780 P1 Nov. 29, 2018

(30) Foreign Application Priority Data

May 24, 2017 (CH) ..... PBR 17-3149

(51) Int. Cl.
*A01H 5/02* (2018.01)
*A01H 6/42* (2018.01)

(52) U.S. Cl.
USPC ..... Plt./328
CPC ..... *A01H 6/425* (2018.05)

(58) Field of Classification Search
USPC ..... Plt./263.1, 324, 325, 328
See application file for complete search history.

*Primary Examiner* — Susan McCormick Ewoldt
*Assistant Examiner* — Karen M Redden
(74) *Attorney, Agent, or Firm* — Bethany Reid Roahrig; Cochran Freund & Young LLC

(57) ABSTRACT

A new *pelargonium* plant particularly distinguished by light pink flowers with pink eyes, an upright habit, and good branching, is disclosed.

1 Drawing Sheet

Genus and species: *Pelargonium zonale.*
Variety denomination: 'KLEPZ17487'.

CROSS REFERENCE TO RELATED APPLICATION

The present application claims priority to Switzerland Plant Variety Protection Application No. 17-3149, as filed on May 24, 2017, the entire contents are herein incorporated by reference for all the application teaches and discloses. A European Community Plant Variety Protection Application was filed on May 30, 2017, Application No. 2017/1440.

BACKGROUND OF THE NEW PLANT

The present invention comprises a new and distinct variety of *pelargonium*, botanically known as *Pelargonium zonale* and hereinafter referred to by the variety name 'KLEPZ17487'. 'KLEPZ17487' originated from an open pollination in June 2012 in Stuttgart, Germany between an unknown male *pelargonium* and the female proprietary *pelargonium* variety PIP-2012-8901 (unpatented).

Seeds from the open pollination were obtained and sown and plants were grown for evaluation. A single plant was selected in June 2013 and subsequently named 'KLEPZ17487'. In September 2013 'KLEPZ17487' was first vegetatively propagated in Stuttgart, Germany by vegetative cuttings from branches. 'KLEPZ17487' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Light pink with pink eye flowers;
2. Upright habit; and
3. Good branching.

DESCRIPTION OF THE PHOTOGRAPH

This new *pelargonium* plant is illustrated by the accompanying photograph which shows an overall view of the plant. The photograph is of an approximately 10 week old plant old plant grown in Stuttgart, Germany under glasshouse conditions in November 2016. The colors shown are as true as can be reasonably obtained by conventional photographic procedures.

DESCRIPTION OF THE NEW VARIETY

The following detailed descriptions set forth the distinctive characteristics of 'KLEPZ17487'. The data which define these characteristics were collected from asexual reproductions carried out in Stuttgart, Germany. Data was collected on plants grown three months after planting in Stuttgart, Germany under a glass covered greenhouse in April 2018. Color references are to The R.H.S. Colour Chart of The Royal Horticultural Society of London (R.H.S.), 5$^{th}$ edition (2007).

Classification:
*Family.*—Geraniaceae.
*Botanical.—Pelargonium zonale.*
*Common.—Pelargonium.*
*Designation.*—'KLEPZ17487'.

Parentage:
*Female.*—PIP-2012-8901 (unpatented).
*Male.*—Unknown.

Plant:
*Form*.—Bushy and mounding.
*Habit*.—Upright.
*Height*.—14.0 cm.
*Spread*.—19.5 cm.
*Natural flowering season*.—April to October.
*Propagation type*.—Vegetative cuttings.
*Time to produce a finished flowering plant*.—3 months.
*Time to initiate and develop roots*.—4 weeks.
*Root description*.—White, dense, and fine.

Stems:
*Quantity of stems per plant*.—3 to 5.
*Color*.—RHS 144A.
*Surface texture*.—Moderately pubescent.
*Stem form*.—Round.
*Diameter*.—0.6 cm to 1.0 cm.
*Length*.—9.0 cm to 12.0 cm.
*Internode length*.—1.0 cm to 3.0 cm.
*Anthocyanin*.—Absent.

Leaves:
*Arrangement*.—Alternate.
*Shape*.—Reniform.
*Apex*.—Round.
*Base*.—Slightly open.
*Margin*.—Crenate.
*Texture* (*both surfaces*).—Moderately pubescent.
*Length*.—4.0 cm to 6.0 cm.
*Width*.—6.0 cm to 9.0 cm.
*Color*.—Upper surface: RHS 137B. Lower surface: RHS 138A.
*Zonation*.—Absent.
*Petiole*.—Length: 4.0 cm to 5.0 cm. Diameter: 0.3 cm to 0.4 cm. Color: RHS 138A. Strength: Moderate.
*Venation pattern*.—Palmate.
*Venation color*.—Upper surface: RHS 137B. Lower surface: RHS 138B.

Inflorescence:
*Lastingness of flowers on the plant*.—2 weeks.
*Umbels*.—Quantity of umbels per plant: 6 to 7. Length: 6.5 cm. Diameter: 11.0 cm.
*Individual florets of the umbel*.—Quantity of florets per umbel: 8 to 16. Depth: 2.5 cm. Diameter: 4.5 cm.
*Fragrance*.—Absent.

Flower buds:
*Cluster shape*.—Round.
*Cluster size*.—Length: 1.5 cm. Width: 2.0 cm.
*Surface texture*.—Sparsely pubescent.
*Bud*.—Height: 0.5 cm to 1.0 cm. Width: 0.4 cm to 0.5 cm. Shape: Elliptic. Apex: Acute. Base: Obtuse. Margin: Entire. Color: RHS 138B.

Petals:
*Quantity per flower*.—5.
*Shape*.—Spatulate.
*Apex*.—Round.
*Base*.—Obtuse.
*Margin*.—Entire.
*Length*.—3.0 cm.
*Width*.—2.7 cm.
*Texture* (*both surfaces*).—Smooth.
*Color of lobes*.—Upper lobes: Upper surface: Border of 1.0 cm colored RHS 62D, eye of 1.5 cm colored RHS N57A. Lower surface: RHS 62D. Lower lobes: Upper surface: Border of 1.0 cm colored RHS 62D, eye of 1.5 cm colored RHS N57A. Lower surface: RHS 62D.

Petaloids: Absent.

Sepals:
*Number per flower*.—5.
*Shape*.—Elliptic.
*Apex*.—Acute.
*Base*.—Obtuse.
*Margin*.—Entire.
*Surface texture*.—Upper surface: Smooth. Lower surface: Sparsely pubescent.
*Color* (*both surfaces*).—RHS 138B.
*Length*.—1.5 cm.
*Width*.—0.5 cm.

Pedicel:
*Length*.—3.0 cm.
*Diameter*.—0.2 cm.
*Color*.—RHS 138B.
*Surface texture*.—Sparsely pubescent.
*Strength*.—Moderate.

Peduncle:
*Length*.—9.0 cm.
*Diameter*.—0.5 cm.
*Color*.—RHS 138A.
*Surface texture*.—Sparsely pubescent.
*Strength*.—Moderate.

Reproductive organs:
*Stamens*.—Quantity of stamens per flower: 6. Anther length: 0.2 cm. Filament length: 0.3 cm. Filament color: RHS 62D. Pollen amount: Moderate. Pollen color: RHS 28A.
*Pistils*.—Number: 1. Stigma color: RHS 38A. Style length: 0.2 cm. Style color: RHS 38A. Ovary arrangement: Central. Ovary color: RHS 138B. Ovary diameter: 0.2 cm. Ovary length: 0.4 cm.

Fruit and seed set: None observed.

Disease and pest/insect resistance: None observed.

COMPARISON WITH PARENTAL LINE AND KNOWN VARIETY

'KLEPZ17487' is distinguished from its female parent as described in Table 1:

TABLE 1

Comparison with Female Parental Line

| Characteristic | 'KLEPZ17487' | Female PIP-2012-8901 |
|---|---|---|
| Flower Color | Light pink with a pink eye | Pink |
| Vigour | Medium | Strong |

'KLEPZ17487' can be compared to the commercial variety AMERICANA 'White Splash', (U.S. Plant Pat. No. 9,317). Differences between the two varieties are described in Table 2:

TABLE 2

Comparison with Similar Variety

| Characteristic | 'KLEPZ17487' | Commercial line AMERICANA 'White Splash' |
|---|---|---|
| Flower Color | Light pink with a pink eye | White with a pink eye |
| Branching | Good | Low |

We claim:

1. A new and distinct variety of *pelargonium* plant named 'KLEPZ17487' as illustrated and described herein.

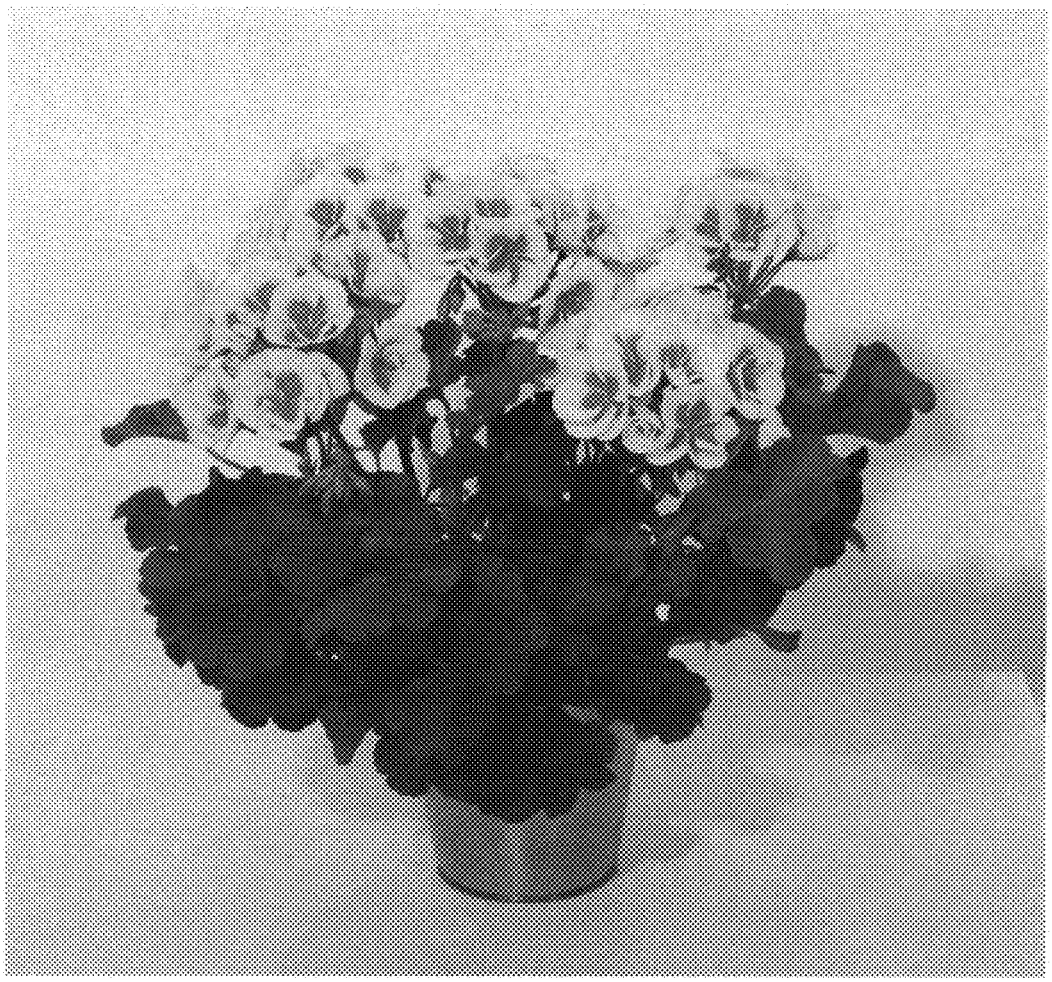

* * * * *